(12) United States Patent
Starz et al.

(10) Patent No.: US 10,814,141 B2
(45) Date of Patent: Oct. 27, 2020

(54) DEVICE FOR ADMINISTERING A RADIOPHARMACEUTICAL DRUG

(71) Applicant: ASSISTANCE PUBLIQUE-HOPITAUX DE PARIS, Paris (FR)

(72) Inventors: Christian Starz, Butry-sur-oise (FR); Philippe Darras, Aisy-sur-armencon (FR); Hervé Caradec, Champs-sur-marne (FR); Makrem Ben Reguiga, Paris (FR)

(73) Assignee: ASSISTANCE PUBLIQUE-HOPITAUX DE PARIS, Paris (FR)

( * ) Notice: Subject to any disclaimer, the term of this patent is extended or adjusted under 35 U.S.C. 154(b) by 241 days.

(21) Appl. No.: 15/775,557

(22) PCT Filed: Nov. 15, 2016

(86) PCT No.: PCT/EP2016/077657
§ 371 (c)(1),
(2) Date: May 11, 2018

(87) PCT Pub. No.: WO2017/085038
PCT Pub. Date: May 26, 2017

(65) Prior Publication Data
US 2018/0345037 A1 Dec. 6, 2018

(30) Foreign Application Priority Data
Nov. 16, 2015 (FR) ..................... 15 60996

(51) Int. Cl.
*G21F 5/015* (2006.01)
*A61N 5/10* (2006.01)
(Continued)

(52) U.S. Cl.
CPC ........... *A61N 5/1002* (2013.01); *A61M 5/007* (2013.01); *A61M 5/1417* (2013.01); *G21F 1/085* (2013.01);
(Continued)

(58) Field of Classification Search
CPC ................ A61M 5/007; A61M 5/1417; A61N 2005/1021; A61N 2005/1094; A61N 5/1002; G21F 5/015
See application file for complete search history.

(56) References Cited

U.S. PATENT DOCUMENTS 2,533,102 A 12/1950 Gifford
2011/0124948 A1 5/2011 Yokell

FOREIGN PATENT DOCUMENTS

FR 1264753 6/1961
WO 2014188401 A1 11/2014

OTHER PUBLICATIONS

International Search Report, Corresponding International Application, Application No. PCT/EP2016/077657, 6 pages.

*Primary Examiner* — Christine H Matthews
(74) *Attorney, Agent, or Firm* — Cooper Legal Group, LLC; Ronald M. Kachmarik

(57) ABSTRACT

An administration device that includes a hermetic container closed by a cap, containing a radiopharmaceutical medicament, and provided with a protective shield made of a radiopaque material. The device includes a support provided with attachment structure. The container is removably attached to the support in a position allowing access to the cap. The support includes a baseplate provided with an opening allowing access to the cap. A cover and rods connect the baseplate and the cover.

11 Claims, 3 Drawing Sheets

(51) Int. Cl.
  A61M 5/14   (2006.01)
  G21F 1/08   (2006.01)
  A61M 5/00   (2006.01)
  G21F 5/12   (2006.01)
(52) U.S. Cl.
  CPC ............ G21F 5/015 (2013.01); G21F 5/12 (2013.01); *A61N 2005/1021* (2013.01); *A61N 2005/1094* (2013.01)

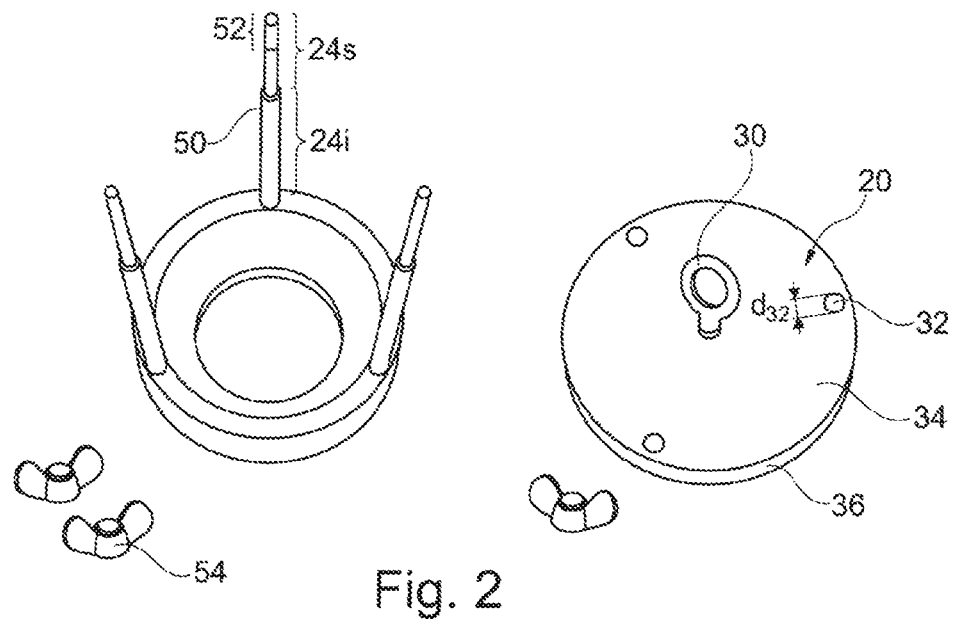
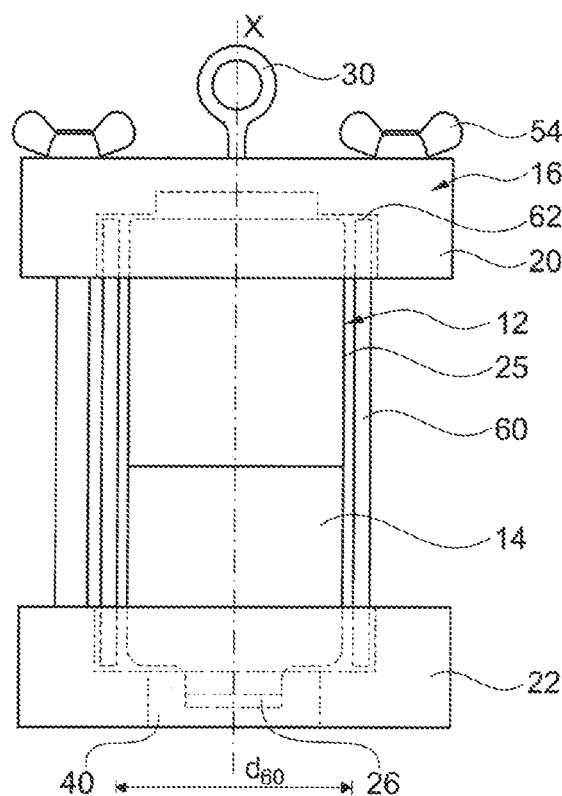

DEVICE FOR ADMINISTERING A RADIOPHARMACEUTICAL DRUG

TECHNICAL FIELD

The present invention relates to a device for administering a radiopharmaceutical medicament, intended to be suspended from a perfusion stand, especially for intravenous injection. The invention also relates to a perfusion stand fitted with such a device.

PRIOR ART

Radiopharmaceutical medicaments intended for metabolic radiotherapy are generally administered by slow intravenous perfusion. These medicaments, conventionally delivered in a container provided with a radiopaque shield, may be transferred into a syringe, then administered with a syringe driver. However, this procedure exposes personnel to risks of irradiation.

The aim of the present invention is to provide an administration device that makes it possible to limit this risk.

SUMMARY OF THE INVENTION

The invention proposes an administration device comprising
- a hermetic container closed by a cap, containing a radiopharmaceutical medicament, and provided with a protective shield made of a radiopaque material, and
- a support provided with attachment means, the container being removably attached to the support in a position allowing access to said cap.

As will be seen in more detail in the remainder of the description, the device can be easily handled and installed on a perfusion stand. In addition, access to the container is possible through the support, which facilitates setting up die perfusion. Finally, the exposure of personnel to radioactive emissions is limited.

An administration device according to the invention may further comprise one or more of the following optional characteristics:
- the device comprises a single container;
- the protective shield comprises lead and/or tungsten;
- the attachment means comprise a ring;
- the container comprises a receptacle, preferably a single receptacle, of constant thickness;
- the attachment means are attached to a cover of the support;
- the radiopharmaceutical medicament is suitable for metabolic radiotherapy or for a diagnostic application;
- the support comprises a baseplate provided with an opening allowing access to said cap;
- the support comprises a cover, a baseplate and rods connecting the cover and the baseplate, the container extending between the cover and the baseplate;
- at least one end of one of said rods, preferably of each of said rods, can be detached from the cover or from the support to which it is attached, preferably manually;
- the container extends in the space between the cover, the baseplate and the rods;
- the support comprises a cover provided with holes through which rods attached on the baseplate pass,
- the rods comprise stops against which the cover bears by gravity;
- at least one, preferably each, rod has, at its free end, a threaded portion which protrudes above the cover and onto which a nut is screwed so as to bear against the cover;
- the device comprises a preferably transparent cylinder resting on the support and in which the container is housed;
- the height of the cylinder is determined such that the bottom of the container bears against the cover.

The invention also proposes a perfusion apparatus comprising a perfusion stand and an administration device according to the invention, suspended from said stand.

The perfusion stand may comprise wheels and preferably means for blocking said wheels.

The perfusion apparatus may further comprise an injection device, comprising an injection needle and a catheter that brings the radiopharmaceutical medicament leaving the container into fluidic contact with said injection needle. The injection device preferably comprises a perfusion cannula connected to the catheter and passing through the cap closing the container.

BRIEF DESCRIPTION OF THE FIGURES

Other features and advantages of the invention will become further apparent on reading the following detailed description and on examining the appended drawing, in which:

FIG. 2 represents the disassembled support of the device of FIG. 1, the cylinder not being represented;

FIG. 3 represents a side view of the device of FIG. 1; and

Figure 4:
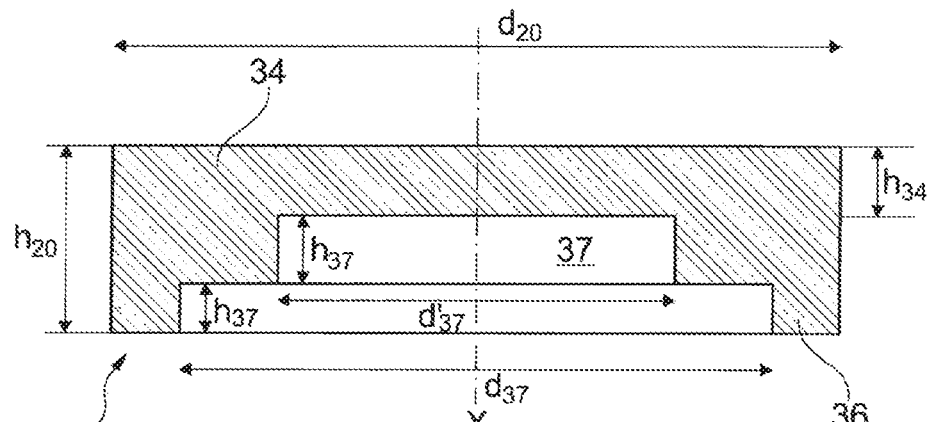
FIGS. 4 and 5 represent, in median cross section, the cover and the baseplate of the support of the device of FIG. 1.

For the sake of simplicity, the suspension ring 30 has not been represented in FIG. 4.

Definitions

A "radiopaque" material is a material able to at least partially filter and/or reduce the radioactive radiation emitted by the radiopharmaceutical medicament, and in particular the photon or particle radiation.

Unless indicated otherwise, "comprising", "containing", "having", "including", or variations thereof, correspond to non-exclusive inclusion.

The description of the figures is made with reference to a vertical direction V. In particular, the adjectives "lower", "upper", "horizontal" and "vertical" refer to this direction.

Figure 1:
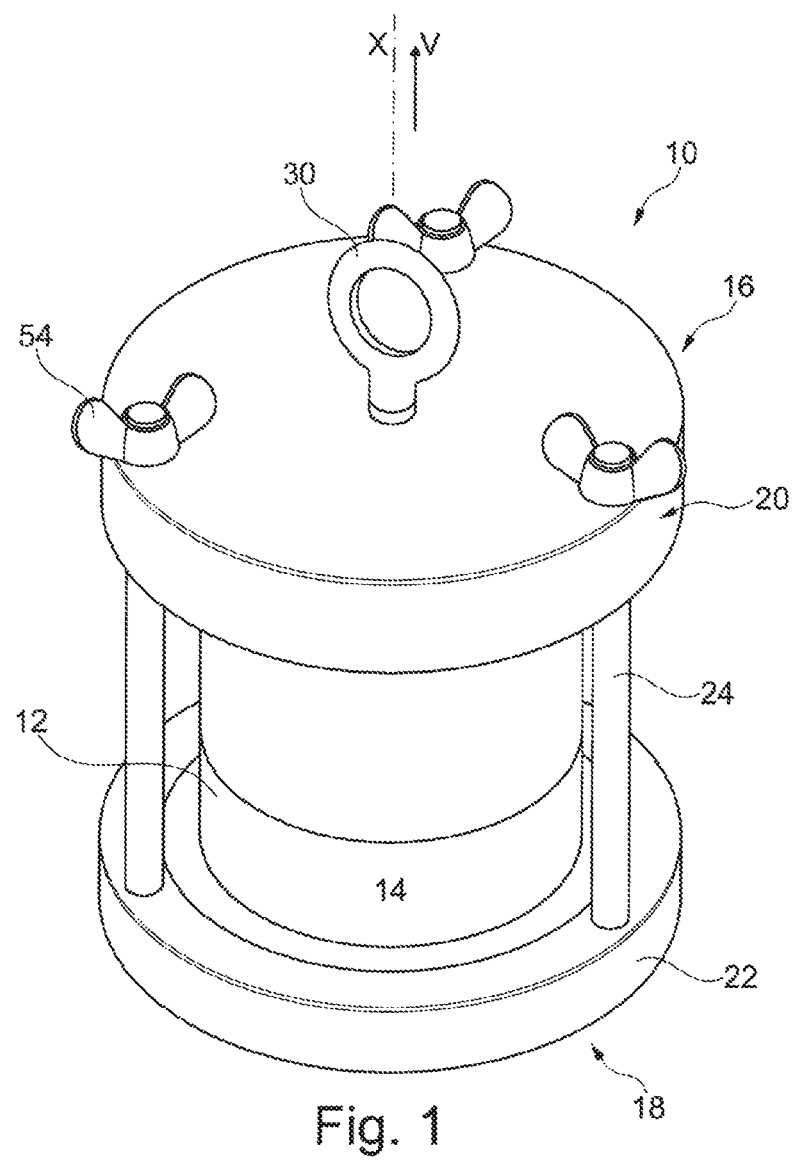
FIG. 1 represents a perspective view of an administration device in a preferred embodiment of the invention.

"Transverse" refers to a direction or to a plane perpendicular to the axis X of the device. Unless indicated otherwise, the pieces are described in the assembled position, as represented in FIG. 1.

DETAILED DESCRIPTION

As illustrated in the figures, an administration device 10 according to the invention comprises a container 12 containing a radiopharmaceutical medicament 14, and a support 16 carrying the container 12. The support 16 comprises a base 18 and a cover 20. The base 18 consists of a baseplate 22 and three rods 24.

The container 12 is a container conventionally used for containing a radiopharmaceutical medicament. More specifically, it comprises a receptacle 25 closed by a cap 26 and provided with a protective shield made of a radiopaque material. In the service position represented in FIG. 1 or in FIG. 3, the container 12 is arranged upside-down, the cap being at the bottom, in order for the medicament to be able to flow by gravity into a cannula, not shown, that passes through the cap.

The radiopaque protective shield, also referred to as "leaded jar" or "vial shield" may be, for example, made of lead, of tungsten, of a leaded glass, of a lead/PMMA (Plexiglas) sandwich, of a tungsten/PMMA sandwich, or of a mixture of these constituents.

Preferably, the protective shield is adapted to filter more than 50%, preferably more than 70%, preferably more than 80%, preferably more than 90%, preferably more than 95%, preferably substantially 100% of the radioactive radiation emitted by the radiopharmaceutical medicament 14.

The radiopharmaceutical medicament 14 may in particular be suitable for metabolic radiotherapy. The radiopharmaceutical medicament may be in particular Quadramet®, Metastron®, therapeutic MIBG®, diagnostic MIBG®, Adreview®, or Lutathera®.

The radiopharmaceutical medicament 14 may be suitable for a diagnostic application.

As represented in FIG. 2, the cover 20 comprises, in the upper part, substantially in the center thereof, attachment means, for example a hook, preferably a ring 30, adapted for suspending the administration device from a perfusion stand.

The cover 20 preferably has a general disk shape with a vertical axis X.

The diameter $d_{20}$ of the cover 20 is preferably greater than 80 mm, preferably greater than 90 mm, preferably greater than 95 mm, and/or less than 110 mm, preferably less than 105 mm, preferably approximately 99 mm.

The height $h_{20}$ of the cover 20 (measured along the vertical axis X) is preferably greater than 15 mm, greater than 20 mm and/or less than 30 mm, less than 25 mm, preferably approximately 23 mm.

The cover 20 preferably comprises an upper wall 34, substantially horizontal in the assembled position represented in FIG. 1, encircled by a lower rim 36, extending substantially vertically under the upper wall 34.

The height $h_{34}$ of the upper wall 34 is preferably greater than 5 mm and/or less than 10 mm, preferably approximately 8 mm.

The cover 20 is provided with substantially vertical holes 32, arranged at the periphery thereof, passing through the thickness thereof, and equiangularly distributed around the axis X.

Each hole 32 has a diameter $d_{32}$ that is slightly larger than that of the upper part of a rod 24. This diameter is preferably greater than 5 mm, greater than 6 mm, greater than 7 mm and/or less than 10 mm, less than 9 mm, less than 8 mm. In a preferred embodiment, the diameter of each of the holes 32 is identical.

Preferably, the holes 32 are made through the rim 36.

The rim 36 and the upper wall 34 define a basin 37 which preferably has a bank with a notched profile, as represented in FIG. 4. The profile of the basin 37 is preferably of revolution around the axis X.

From the bottom to the top, the inside diameter of the basin may in particular be equal to a diameter $d_{37}$ greater than 70 mm, preferably greater than 75 mm and/or less than 90 mm, preferably less than 85 mm, preferably approximately 81 mm, then equal to a diameter $d'_{37}$ greater than 45 mm, greater than 50 mm and/or less than 65 mm, less than 60 mm, preferably approximately 55 mm.

The height $h_{37}$ of at least one, preferably of each step of the notched profile is preferably greater than 5 mm and less than 10 mm, for example 7 or 8 mm.

The container 12 is placed on the baseplate 22 of the base 18. The baseplate 22 has a general annular shape with axis X.

The diameter $d_{22}$ of the baseplate 22 is preferably greater than 80 mm, preferably greater than 90 mm, preferably greater than 95 mm, and/or less than 110 mm, preferably less than 105 mm, preferably approximately 99 mm. It is preferably substantially identical to the outer diameter $d_{20}$ of the cover.

The height $h_{22}$ of the baseplate 22 (measured along the vertical axis X) is preferably greater than 15 mm, greater than 20 mm, and/or less than 30 mm, less than 25 mm, preferably approximately 23 mm.

Figure 5:
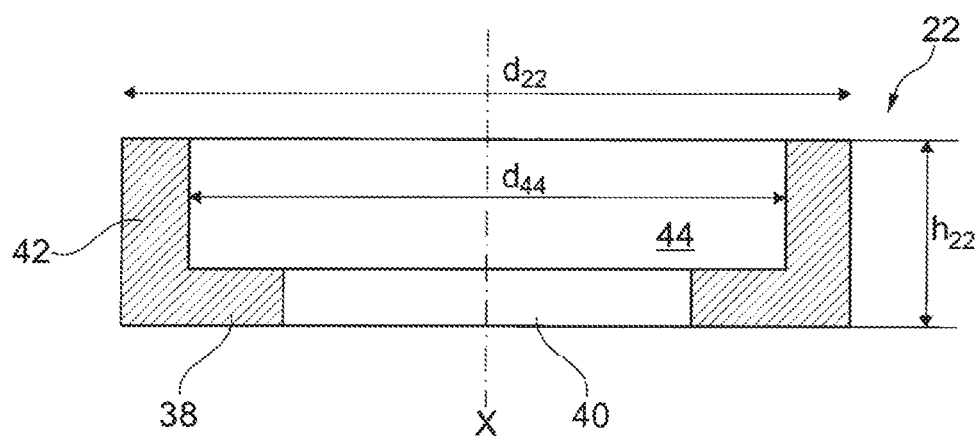

As represented in FIG. 5, the baseplate 22 comprises a bottom 38, pierced with a central opening 40, and an upper rim 42 extending peripherally from the bottom 38 toward the top, substantially along the axis X. The opening 40 is adapted so as to allow access to the container 12, and more specifically to the cap 26 of the container 12, when the latter bears against the bottom 38, as represented in FIG. 3. Advantageously, it is thus easy to pass a perfusion cannula through said cap.

The bottom 38 and the upper rim 42 define a housing 44 for the container 12. The housing 44, preferably substantially cylindrical and with a circular section, has a diameter $d_{44}$ that is preferably substantially identical to the largest diameter $d_{37}$ of the basin 37 of the cover.

The rods 24 are attached substantially vertically to the baseplate 22, preferably in the upper rim 42. They may be attached by any means, for example screwing, welding, force-fitting or interference fitting.

The number of rods 24 and of holes 32 is not limited. It is preferably greater than 2 and/or less than 5, preferably less than 4, preferably three.

The rods 24 are arranged around the axis X so that each of them is able to pass through a hole 32 in the cover. They are preferably equiangularly distributed around the axis X.

In one embodiment, the rods 24 are substantially identical.

Preferably, a rod 24 comprises a lower part $24_i$, the diameter of which is greater than the diameter of the corresponding hole 32, and an upper part $24_s$ having a smaller diameter than the diameter of said hole 32. Advantageously, the transition between the lower part $24_i$ and the upper part $24_s$ defines a rim forming a stop 50 for the cover 20.

The upper part 24 comprises a threaded end portion 52 which, in the position in which the cover is stopped against the stop 50, at least partially protrudes above the upper wall 34 of the cover. Nuts 54, preferably wing nuts, may then be screwed onto the threaded portion 52 in order to clamp the cover against the stop 50.

The cover and/or the baseplate and/or the rods may, for example, be made of steel or of aluminum.

In one embodiment, the administration device further comprises a cylinder 60, preferably of circular section, which, in the assembled position, extends substantially vertically from the baseplate to the cover. The cylinder 60 preferably extends between the rods 24, as represented in FIG. 3.

In one embodiment, the outer diameter of the cylinder 60 is substantially identical to, but slightly smaller than, the diameter $d_{44}$ of the housing 44 of the baseplate 22 and/or one of the inside diameters of the basin 37, which makes it possible to avoid any lateral movement of the cylinder 60 in the assembled position.

The inside diameter $d_{60}$ of the cylinder 60 is preferably adapted such that the cylinder 60 may receive a container 12 while laterally immobilizing same. In other words, the largest transverse dimension of the container 12 is preferably slightly smaller than the inside diameter $d_{60}$ of the cylinder 60.

If the cylinder goes beyond the level of the stop 50, the cover bears against the upper edge 62 of the cylinder, and no longer against stop 50. The position, along the axis X, of the cover 20 relative to the baseplate 22, may then be modified simply by changing the cylinder 60.

Of course, the length of the threaded portion 52 must consequently be adapted.

The invention also relates to an assembly comprising an administration device according to the invention and several cylinders 60 having different heights and/or different inside diameters $d_{60}$.

Preferably, these inside diameters $d_{60}$ and heights are adapted to outside diameters and heights of commercially available containers 12.

The cylinder 60 preferably has a radiopaque wall.

The cylinder 60 is preferably transparent, so that the container 12 can be seen and especially so that the filling level thereof can be verified.

The administration device is operated as follows, in the preferred embodiment.

The device is initially in the disassembled position represented in FIG. 2.

A cylinder 60 having an inside diameter that is slightly larger than that of the container 12 is placed on the baseplate, between the rods 24. It is laterally immobilized in the housing 44.

The container 12 containing the radiopharmaceutical medicament is introduced, with its radiopaque shield, into the cylinder 60 and placed upside-down so as to bear by gravity against the baseplate 22. The inside diameter of the cylinder 60 is slightly larger than the outside diameter of the container 12, which makes it possible to hold the container 12 in position perfectly. The cap is accessible through the opening 40, as represented in FIG. 3.

The cover 20 is then arranged such that the rods 24 are introduced into the holes 32 until they pass beyond the upper wall 34.

The wing nuts 54 are then screwed onto the rods 24, so as to push the cover 16 against the cylinder 60 or against the stops 50, depending on whether the height of the cylinder goes beyond the stops 50 or not.

The height of the cylinder is preferably determined such that, in the assembled position represented in FIG. 1, the bottom of the container bears against the cover 20.

Advantageously, the container therefore does not move back towards the cover when the perfusion cannula is introduced through the cap 26.

The opening 40 advantageously makes it possible to introduce a perfusion cannula through the cap 26 in order to extract the medicament. The administration device formed in this way may be suspended from a perfusion stand by the ring 30.

Advantageously, the medicament remains packaged in its original packaging, namely the container 12, which avoids any risk of irradiation of personnel. In addition, the setting up of the container 12 between the cover 20 and the baseplate 22 is quick and practical. Finally, it is held in position effectively between the baseplate, the cover and the cylinder 60.

The device is then suspended from a perfusion stand by the ring 30.

Of course, the invention is not limited to the embodiments described and represented that are provided solely by way of illustrative examples.

In particular, the rods could be attached to the cover. The rods could pass through holes made in the baseplate and preferably have a threaded portion at their lower free end, a nut being screwed onto said threaded portion and the baseplate resting on said nut.

The invention claimed is:

1. An administration device comprising
   a hermetic container closed by a cap, containing a radiopharmaceutical medicament, and provided with a protective shield made of a radiopaque material, and
   a support provided with attachment means, the container being removably attached to the support in a position allowing access to said cap,
   wherein the support comprises a baseplate provided with an opening allowing access to said cap, a cover and rods connecting the baseplate and the cover, the container extending between the cover and the baseplate.

2. The device as claimed in claim 1, wherein the protective shield comprises lead and/or tungsten.

3. The device as claimed in claim 1, wherein the attachment means comprise a ring.

4. The device as claimed in 1, wherein the cover is provided with holes through which the rods pass, the rods being attached on the baseplate.

5. The device as claimed in claim 1, wherein the rods comprise stops which the cover bears by gravity.

6. The device as claimed in claim 1, wherein at least one, rod of the rods has a free end and has, at said free end, a threaded portion which protrudes above the cover and onto which a nut is screwed so as to bear against the cover.

7. The device as claimed in claim 1, comprising a cylinder resting on the support and in which the container is housed.

8. The device as claimed in claim 7, wherein the container has a bottom, and the height of the cylinder is determined such that the bottom of the container bears against the cover.

9. The device as claimed in claim 7, wherein the cylinder is transparent, so that the container can be seen.

10. A perfusion apparatus comprising a perfusion stand and an administration device as claimed in claim 1, suspended from said stand.

11. An assembly comprising
    an administration device as claimed in claim 1, and
    several cylinders having different heights and/or different inside diameters and which are adapted to be able to be sandwiched between the baseplate and the cover of the support.

* * * * *